(12) United States Patent
Landwehr et al.

(10) Patent No.: US 9,306,999 B2
(45) Date of Patent: Apr. 5, 2016

(54) INTERACTIVE SESSIONS WITH PARTICIPANTS AND PROVIDERS

(71) Applicant: UNITEDHEALTH GROUP INCORPORATED, Minnetonka, MN (US)

(72) Inventors: Brian R. Landwehr, Minnetonka, MN (US); Cullen Davis, Minnetonka, MN (US); Sandy Johnson, Minnetonka, MN (US); Arrianne Hoyland, Minnetonka, MN (US); Shane Huston, Minnetonka, MN (US); David Kaminski, Minnetonka, MN (US); Robert Plourde, Minnetonka, MN (US); Timothy Arnal, Minnetonka, MN (US); Andrew Chester, Minnetonka, MN (US)

(73) Assignee: UNITEDHEALTH GROUP INCORPORATED, Minnetonka, MN (US)

( * ) Notice: Subject to any disclaimer, the term of this patent is extended or adjusted under 35 U.S.C. 154(b) by 424 days.

(21) Appl. No.: 13/912,824

(22) Filed: Jun. 7, 2013

(65) Prior Publication Data

US 2013/0332616 A1    Dec. 12, 2013

Related U.S. Application Data

(60) Provisional application No. 61/657,352, filed on Jun. 8, 2012.

(51) Int. Cl.
*G06F 15/16* (2006.01)
*H04L 29/06* (2006.01)
(Continued)

(52) U.S. Cl.
CPC ............ *H04L 65/60* (2013.01); *H04L 67/12* (2013.01); *G06F 19/322* (2013.01); *G06F 19/3425* (2013.01)

(58) Field of Classification Search
CPC ......... H04L 65/40; H04L 65/60; H04L 67/12; G06F 17/30811; G06F 19/322; G06F 19/3425
USPC ................................. 709/204, 205, 217, 219
See application file for complete search history.

(56) References Cited

U.S. PATENT DOCUMENTS 8,050,461 B2   11/2011   Shpunt et al.
8,166,421 B2    4/2012   Magal et al.
(Continued)

FOREIGN PATENT DOCUMENTS

WO    WO 2008/007292 A1    1/2008

OTHER PUBLICATIONS

International Searching Authority, International Search Report and Written Opinion for International Application No. PCT/US2013/044654, mailed Nov. 20, 2013, 11 pages, European Patent Office, The Netherlands.

(Continued)

*Primary Examiner* — Viet Vu
(74) *Attorney, Agent, or Firm* — Alston & Bird LLP

(57) ABSTRACT

Computer program products, methods, systems, apparatus, and computing entities are provided for sessions with participants and providers. For example, in one embodiment, a provider can interact with multiple participants to conduct interactive treatment sessions. Further, a participant can interact with multiple providers to conduct interactive treatment sessions. For the interactive treatment sessions, motion data and video data of the participant can be simultaneously displayed to the provider.

15 Claims, 16 Drawing Sheets

(51) Int. Cl.
*H04L 29/08* (2006.01)
*G06F 19/00* (2011.01)

(56) References Cited

U.S. PATENT DOCUMENTS

| | | | |
|---|---|---|---|
| 2007/0190506 A1 | 8/2007 | Jeng et al. | |
| 2008/0146302 A1* | 6/2008 | Olsen | A63F 13/12 463/7 |
| 2009/0033770 A1 | 2/2009 | Johnson | |
| 2009/0299232 A1 | 12/2009 | Lanfermann et al. | |
| 2010/0049095 A1* | 2/2010 | Bunn | A61B 5/1038 600/595 |
| 2011/0025827 A1 | 2/2011 | Shpunt et al. | |
| 2011/0072037 A1* | 3/2011 | Lotzer | G06F 17/30855 707/769 |
| 2011/0158508 A1 | 6/2011 | Shpunt et al. | |
| 2011/0211754 A1 | 9/2011 | Litvak et al. | |
| 2013/0060914 A1* | 3/2013 | Callahan | G08B 5/00 709/219 |
| 2013/0063579 A1* | 3/2013 | Hanina | A61B 1/00 348/61 |

OTHER PUBLICATIONS

Accenture, "Basque Country: Managing Increased Chronicity Through Public Health Transformation," 2013, 4 pages, Retrieved from <http://www.accenture.com/SiteCollectionDocuments/PDF/Accenture-Basque-Country-Managing-Increased-Chronicity-Through-Public-Health-Transformation.pdf>, on Jun. 6, 2013.

PALOMITO79, "Teki Kinect Accenture Osakidetza English.mp4," *YouTube*, <http://www.youtube.com/watch?v=VkFlu7pO7zc>, May 16, 2012.

International Preliminary Examining Authority, Written Opinion (second) for International Application No. PCT/US2013/044654, mailed Jun. 16, 2014, 7 pages, European Patent Office, Germany.

International Preliminary Examining Authority, International Preliminary Report on Patentability for International Application No. PCT/US2013/044654, mailed Oct. 9, 2014, 22 pages, European Patent Office, Germany.

\* cited by examiner

| Evidence Informed Treatment | Low Risk | Medium Risk | High Risk |
|---|---|---|---|
| | Remain Active | Manipulation | Biopsychosocial assessment |
| | Hot Packs | Specific Exercise | Close gaps in participant knowledge |
| | OTC | Therapies | Emphasize active self-management |
| | Watchful Waiting | Acupuncture | Focus on psychological prognostic factors |
| Primary Care Giver | None | DC | Providers most effective with Medium Risk participants, but are also trained to address cognitive issues |
| | Health Coach, Nurseline, online resources | PT | |
| Participant Motivation | High – many options | High – many options | Moderate – may not seek/comply with plan |

Fig. 5

INTERACTIVE SESSIONS WITH PARTICIPANTS AND PROVIDERS

CROSS-REFERENCE TO RELATED APPLICATIONS

This application claims priority to U.S. Application No. 61/657,352 filed on Jun. 8, 2012, the contents of which are hereby incorporated in their entirety by reference.

BACKGROUND

Emerging technologies have increased the ability of healthcare, occupational therapy, education providers and the like to take advantage of various telecommunication and information technologies to, for example, provide care, therapy, or education to various participants, while remote from such participants. However, a need still exists to provide for real-time management alteration of treatment and education regimens tied to motion-capture-tracked physical activity and reporting.

BRIEF SUMMARY

In general, embodiments of the present invention provide methods, apparatus, systems, computing devices, computing entities, and/or the like for interactive treatment sessions.

In accordance with one aspect, a method is provided. In one embodiment, the method comprises establishing an interactive session between a participant computing entity and a provider computing entity, (a) the interactive session for a user of the participant computing entity to perform a treatment during the interactive session, (b) the interactive session comprising a video stream of video data and a motion stream of motion data originating from the participant computing entity and provided to the provider computing entity, (c) the video data of the video stream comprising video of the user performing the treatment during the interactive session, (d) the motion data of the motion stream comprising motions of the user performing the treatment during the interactive session, and (e) the video data and the motion data to be displayed simultaneously by the provider computing entity.

In accordance with another aspect, a computer program product is provided. The computer program product may comprise at least one computer-readable storage medium having computer-readable program code portions stored therein, the computer-readable program code portions comprising executable portions configured to establish an interactive session between a participant computing entity and a provider computing entity, (a) the interactive session for a user of the participant computing entity to perform a treatment during the interactive session, (b) the interactive session comprising a video stream of video data and a motion stream of motion data originating from the participant computing entity and provided to the provider computing entity, (c) the video data of the video stream comprising video of the user performing the treatment during the interactive session, (d) the motion data of the motion stream comprising motions of the user performing the treatment during the interactive session, and (e) the video data and the motion data to be displayed simultaneously by the provider computing entity.

In accordance with yet another aspect, an apparatus comprising at least one processor and at least one memory including computer program code is provided. In one embodiment, the at least one memory and the computer program code may be configured to, with the processor, cause the apparatus to establish an interactive session between a participant computing entity and a provider computing entity, (a) the interactive session for a user of the participant computing entity to perform a treatment during the interactive session, (b) the interactive session comprising a video stream of video data and a motion stream of motion data originating from the participant computing entity and provided to the provider computing entity, (c) the video data of the video stream comprising video of the user performing the treatment during the interactive session, (d) the motion data of the motion stream comprising motions of the user performing the treatment during the interactive session, and (e) the video data and the motion data to be displayed simultaneously by the provider computing entity.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIGS. 5-16 are exemplary input and output produced by various embodiments of the present invention.

DETAILED DESCRIPTION

Figure 1:
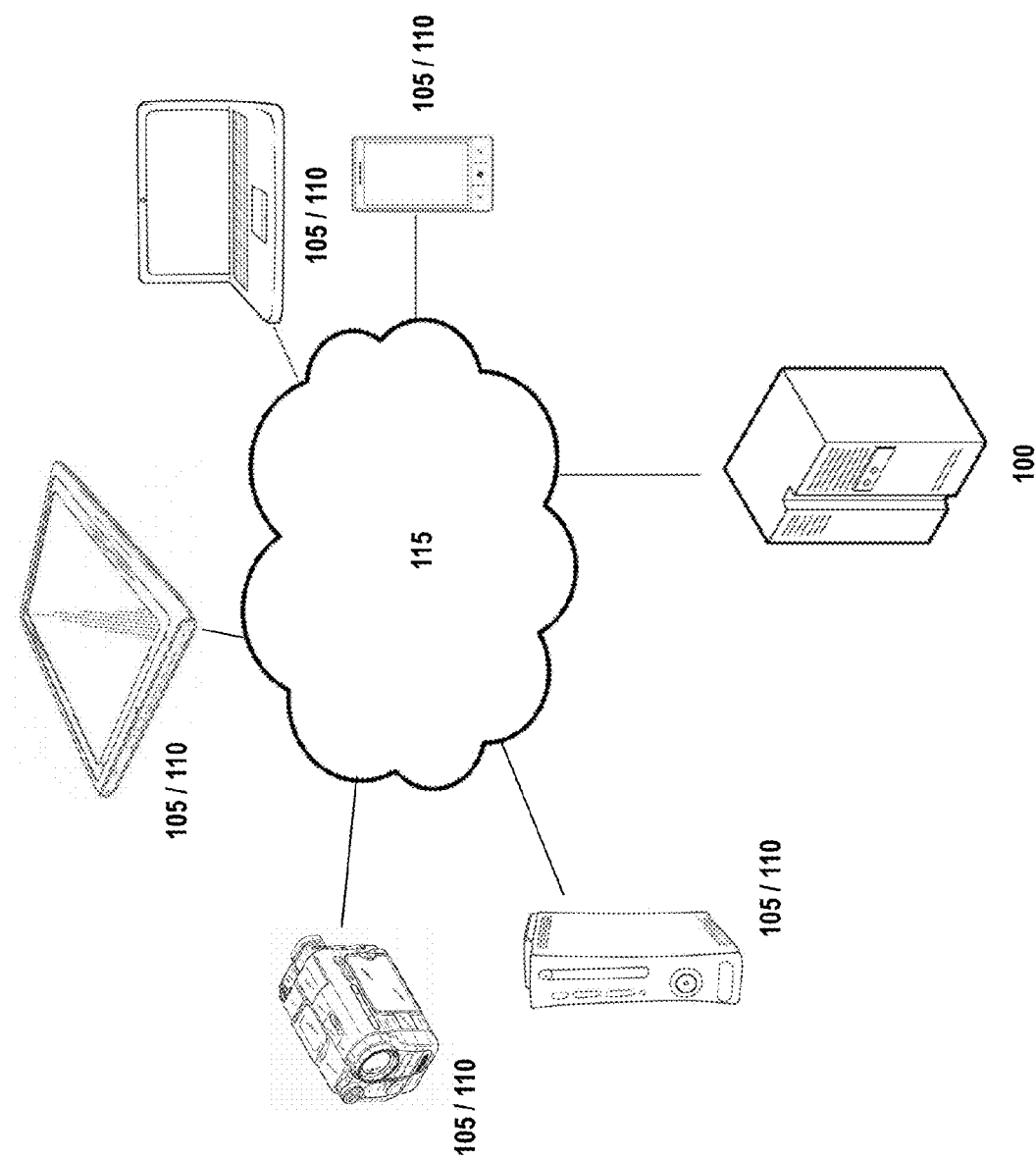
FIG. 1 is an overview of a system that can be used to practice embodiments of the present invention.

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory, multimedia memory cards (MMC), secure digital (SD) memory cards, Memory Sticks, and/or the like. Further, a non-volatile computer-readable storage medium may also include conductive-bridging random access memory (CBRAM), phase-change random access memory (PRAM), ferroelectric random-access memory (FeRAM), resistive random-access memory (RRAM), Silicon-Oxide-Nitride-Oxide-Silicon memory (SONOS), racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Rambus in-line memory module (RIMM), dual in-line memory module (DIMM), single in-line memory module (SIMM), video random access memory VRAM, cache memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. However, embodiments of the present invention may also take the form of an entirely hardware embodiment performing certain steps or operations.

Embodiments of the present invention are described below with reference to block diagrams and flowchart illustrations. Thus, it should be understood that each block of the block diagrams and flowchart illustrations, respectively, may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of an exemplary embodiment of the present invention. As shown in FIG. 1, this particular embodiment may include one or more management computing entities 100, one or more participant computing entities 105, one or more provider computing entities 110, and one or more networks 115. Each of these components, entities, devices, systems, and similar words used herein interchangeably may be in direct or indirect communication with, for example, one another over the same or different wired or wireless networks. Additionally, while FIG. 1 illustrates the various system entities as separate, standalone entities, the various embodiments are not limited to this particular architecture.

Exemplary Management Computing Entity

Figure 2:
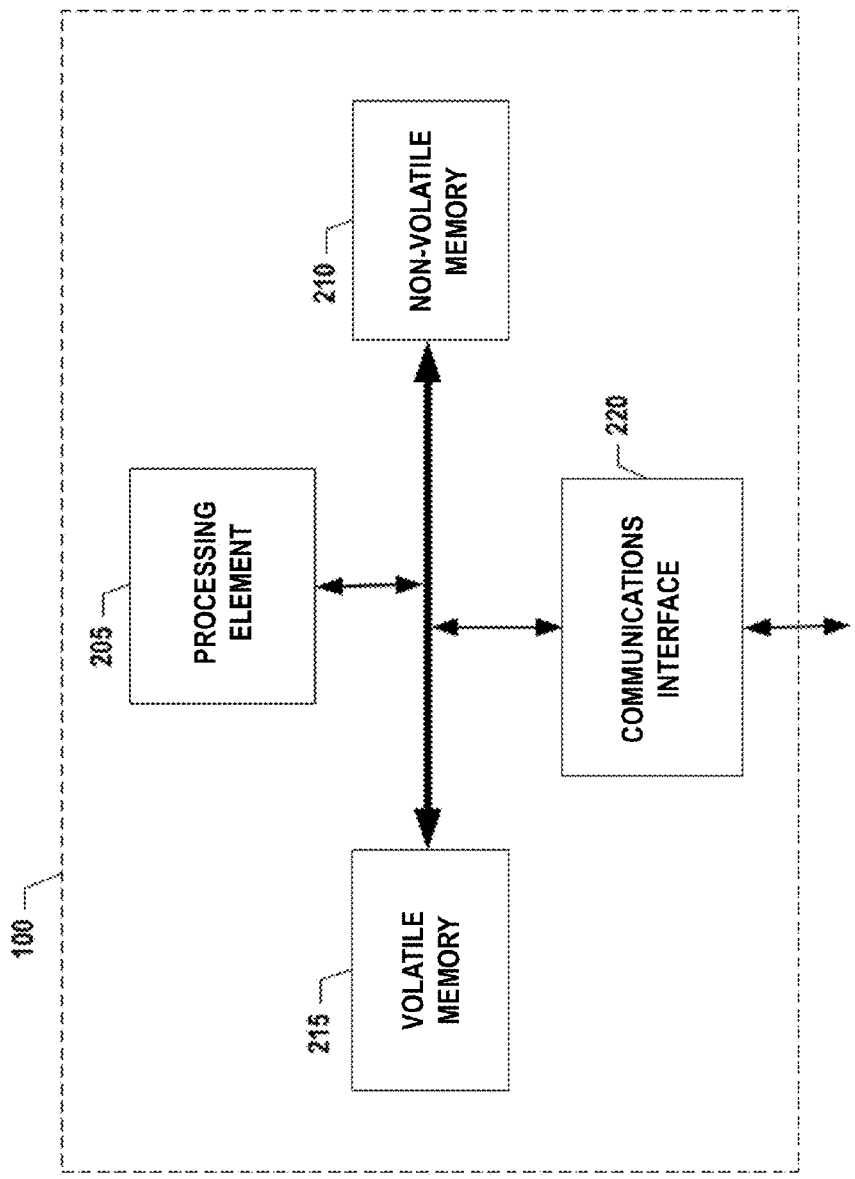
FIG. 2 is an exemplary schematic diagram of a management computing entity according to one embodiment of the present invention.

FIG. 2 provides a schematic of a management computing entity 100 according to one embodiment of the present invention. In some embodiments, the management computing entity 100 may be associated with an organization engaged in healthcare-related services. In general, the terms device, system, computing entity, entity, and/or similar words used herein interchangeably may refer to, for example, one or more computers, computing entities, mobile phones, desktops, tablets, notebooks, laptops, distributed systems, watches, glasses, key fobs, radio frequency identification (RFID) tags, ear pieces, scanners, cameras, wristbands, kiosks, input terminals, servers, gaming consoles (e.g., Xbox, Play Station, Wii), blades, gateways, switches, processing devices, processing entities, relays, routers, network access points, base stations, the like, and/or any combination of devices or entities adapted to perform the functions, operations, and/or processes described herein. The management computing entity 100 may also include, be associated with, and/or be in communication with a participant database, provider database, a web application server, an activity data server, an audio/video server, and/or the like. Thus, reference to the management computing entity 100 may also refer to such systems. Such functions, operations, and/or processes may include, for example, transmitting/providing, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the management computing entity 100 may also include one or more communications interfaces 220 for communicating with various computing entities, such as by communicating data, content, information, and/or similar terms used herein interchangeably that can be transmitted/provided, received, operated on, processed, displayed, stored, and/or the like. For instance, the management computing entity 100 may communicate with participant computing entities 105, provider computing entities 110, and/or various other computing entities.

As shown in FIG. 2, in one embodiment, the management computing entity 100 may include or be in communication with one or more processing elements 205 (also referred to as processors, processing circuitry, and/or similar terms used herein interchangeably) that communicate with other elements within the management computing entity 100 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the management computing entity 100 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a structured collection of records or data that is stored in a computer-readable storage medium, such as via a relational database, hierarchical database, and/or network database.

In one embodiment, the management computing entity 100 may further include or be in communication with volatile media (also referred to as volatile storage, memory, memory storage, memory circuitry and/or similar terms used herein interchangeably). In one embodiment, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the management computing entity 100 with the assistance of the processing element 205 and operating system.

As indicated, in one embodiment, the management computing entity 100 may also include one or more communications interfaces 220 for communicating with participant computing entities 105, provider computing entities, and/or various other computing entities, such as by communicating data, content, information, and/or similar terms used herein interchangeably that can be transmitted/provided, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the management computing entity 100 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth protocols, wireless universal serial bus (USB) protocols, and/or any other wireless protocol.

Although not shown, the management computing entity 100 may include or be in communication with one or more input elements, such as a keyboard input, a mouse input, a touch screen/display input, audio input, pointing device input, joystick input, keypad input, and/or the like. The management computing entity 100 may also include or be in communication with one or more output elements (not shown), such as audio output, video output, screen/display output, motion output, movement output, and/or the like.

As will be appreciated, one or more of the computing entity's 100 components may be located remotely from other management computing entity 100 components, such as in a distributed system. Furthermore, one or more of the components may be combined and additional components performing functions described herein may be included in the management computing entity 100. Thus, the management computing entity 100 can be adapted to accommodate a variety of needs and circumstances.

Exemplary Participant Computing Entity

Figure 3:
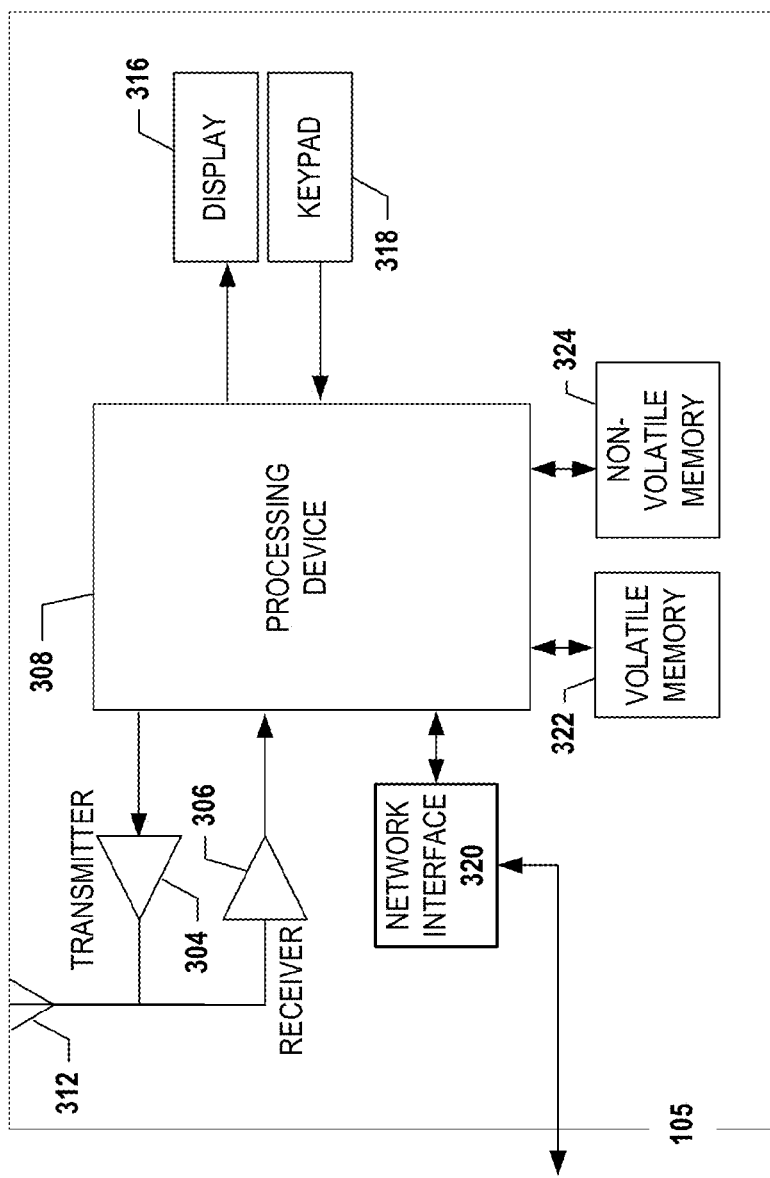
FIG. 3 is an exemplary schematic diagram of a participant or provider computing entity according to one embodiment of the present invention.

In one embodiment, a participant (user) may be any individual who participates in a care program with a provider. Such participants may be health plan members, consumers, customers, patients, students, end users, and/or the like. FIG. 3 provides an illustrative schematic representative of a participant computing entity 105 that can be used in conjunction with embodiments of the present invention. In general, the terms device, system, computing entity, entity, and/or similar words used herein interchangeably may refer to, for example, one or more computers, computing devices, computing entities, gaming consoles (e.g., Xbox, Play Station, Wii), mobile phones, desktops, tablets, notebooks, laptops, distributed systems, watches, glasses, key fobs, RFID tags, ear pieces, scanners, cameras, wristbands, kiosks, input terminals, servers, blades, gateways, switches, processing devices, processing entities, relays, routers, network access points, base stations, the like, and/or any combination of devices or entities adapted to perform the functions, operations, and/or processes described herein. As shown in FIG. 3, the participant computing entity 105 can include an antenna 312, a transmitter 304 (e.g., radio), a receiver 306 (e.g., radio), and a processing element 308 (such as those described above with regard to the management computing entity 100) that provides signals to and receives signals from the transmitter 304 and receiver 306, respectively.

The signals provided to and received from the transmitter 304 and the receiver 306, respectively, may include signaling information in accordance with air interface standards of applicable wireless systems. In this regard, the participant computing entity 105 may be capable of operating with one or more air interface standards, communication protocols, modulation types, and access types. More particularly, the participant computing entity 105 may operate in accordance with any of a number of wireless communication standards and protocols, such as those described above with regard to the management computing entity 100. In a particular embodiment, the participant computing entity 105 may operate in accordance with multiple wireless communication standards and protocols, such as UMTS, CDMA2000, 1xRTT, WCDMA, TD-SCDMA, LTE, E-UTRAN, EVDO, HSPA, HSDPA, Wi-Fi, WiMAX, UWB, IR, Bluetooth, USB, and/or the like.

Via these communication standards and protocols, the participant computing entity 105 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The participant computing entity 105 can also download changes, add-ons, and updates, for instance, to its firmware, software (e.g., including executable instructions, applications, program modules), and operating system.

According to one embodiment, the participant computing entity 105 may include a location determining device and/or functionality. For example, the participant computing entity 105 may include a Global Positioning System (GPS) module adapted to acquire, for example, latitude, longitude, altitude, geocode, course, and/or speed data. In one embodiment, the GPS module acquires data, sometimes known as ephemeris data, by identifying the number of satellites in view and the relative positions of those satellites.

The participant computing entity 105 may also comprise a user interface (that can include a display 316 coupled to a processing element 308) and/or a user input interface (coupled to a processing element 308). For example, the user interface may be an appropriate application, display area, browser, dashboard, user interface, and/or similar words used herein interchangeably executing on and/or accessible via the participant computing entity 105 to interact with and/or cause display of information from the management computing entity 100 and/or provider computing entity 110, as described herein. The user input interface can comprise any of a number of devices allowing the participant computing entity 105 to receive data, such as a keypad 318 (hard or soft), a touch display, voice or motion interfaces, or other input device. In embodiments including a keypad 318, the keypad 318 can include (or cause display of) the conventional numeric (0-9) and related keys (#, *), and other keys used for operating the participant computing entity 105 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The participant computing entity 105 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the participant computing entity 105. As indicated, this may include a participant application that is resident on the entity or accessible through a browser or other user interface for communicating with the management computing entity 100, provider computing entity 110, and/or various other computing entities—including capturing, storing, and providing audio data, video data, and/or motion data.

The participant computing entity 105 may also comprise, be associated with, or be in communication with one or more imaging devices and/or motion capture devices. The terms imaging device, motion capture device, participant computing entity 105, and similar terms are used herein interchangeably. In fact, although described separately, the imaging device and motion capture device may be the same device. In one embodiment, the imaging device may include one or more cameras, one or more laser scanners, one or more infrared scanners, one or more imagers, one or more video cameras, one or more still cameras, one or more Internet Protocol (IP) cameras, and/or the like. The imaging data captured by the imaging devices in zones of interest may be captured using a variety of formats, such as Joint Photographic Experts Group (JPEG), Motion JPEG (MJPEG), Moving Picture Experts Group (MPEG), Graphics Interchange Format (GIF), Portable Network Graphics (PNG), Tagged Image File Format (TIFF), bitmap (BMP), H.264, H.263, Flash Video (FLV), Hypertext Markup Language 5 (HTML5), VP6, VP8, and/or the like.

The motion capture device may regularly, periodically, and/or continuously track the positioning/movement of a scene or one or more markers (e.g., read/receive/collect/capture position data). In one embodiment, the motion capture device may comprise a complementary metal-oxide semiconductor (CMOS) image sensor that reads coded light back from scenes, such as the Kinect for Xbox. The received light can be deciphered to understand the motion that was captured. Such capturing concepts are described in U.S. Pat. Nos. 8,050,461 and 8,166,421 and U.S. Publ. Appl. Nos. 2011-0211754, 2011-0025827, and 2011-0158508, which are incorporated herein in their entireties by reference. In another embodiment, the motion capture device may have infrared cameras capable of reading infrared markers. Such a camera in the motion capture device may be capable of reading various types of light, including visible light and/or ultraviolet light. In one example, a motion capture device may even be part of a gaming console. In another embodiment, the motion capture device may include one or more emitters and phototransistors, for example, in the same housing for emitting radiation and reading the reflected radiation (e.g., reflected from reflective markers). For example, via an emitter, the motion capture device may emit radiation. The reflective markers can reflect the radiation for detection by the motion capture device's phototransistor. As will be recognized, a variety of other approaches and techniques may also be used.

In another embodiment, the participant computing entity 105 may include one or more components that are the same or functionally similar to those of the management computing entity 100, as described in greater detail above.

Exemplary Provider Computing Entity

In one embodiment, a provider (user) may be any doctor, physician assistant, insurance provider, care manager, health provider, trainer, coach, therapist, physical therapist, healthcare-related professional, teacher, and/or similar words used herein interchangeably. In one embodiment, a provider may operate a provider computing entity 110 that includes one or more components that are the same or are functionally similar to those of the management computing entity 100 and/or the participant computing entity 105. For example, in one embodiment, each provider computing entity 110 may include one or more processing elements, one or more display device/input devices (e.g., including user interfaces), volatile and non-volatile storage or memory, one or more image or motion capture devices, and/or one or more communications interfaces. In one embodiment, the user interface may be an appropriate application, display area, browser, dashboard, user interface, and/or similar words used herein interchangeably executing on and/or accessible via the provider computing entity 110 to interact with and/or cause display of information from the management computing entity 100 and/or participant computing entity 105, as described herein. This may also enable to the provider computing entity 110 to communicate with various other computing entities—including capturing, storing, and providing audio data, video data, and/or motion data.

These architectures are provided for exemplary purposes only and are not limiting to the various embodiments. The term computing entity may refer to one or more computers, computing entities, mobile phones, desktops, tablets, notebooks, laptops, distributed systems, watches, glasses, key fobs, RFID tags, ear pieces, scanners, gaming consoles, cameras, wristbands, kiosks, input terminals, servers, blades, gateways, switches, processing devices, processing entities, relays, routers, network access points, base stations, the like, and/or any combination of devices or entities adapted to perform the functions, operations, and/or processes described herein.

III. EXEMPLARY SYSTEM OPERATION

Figure 4:
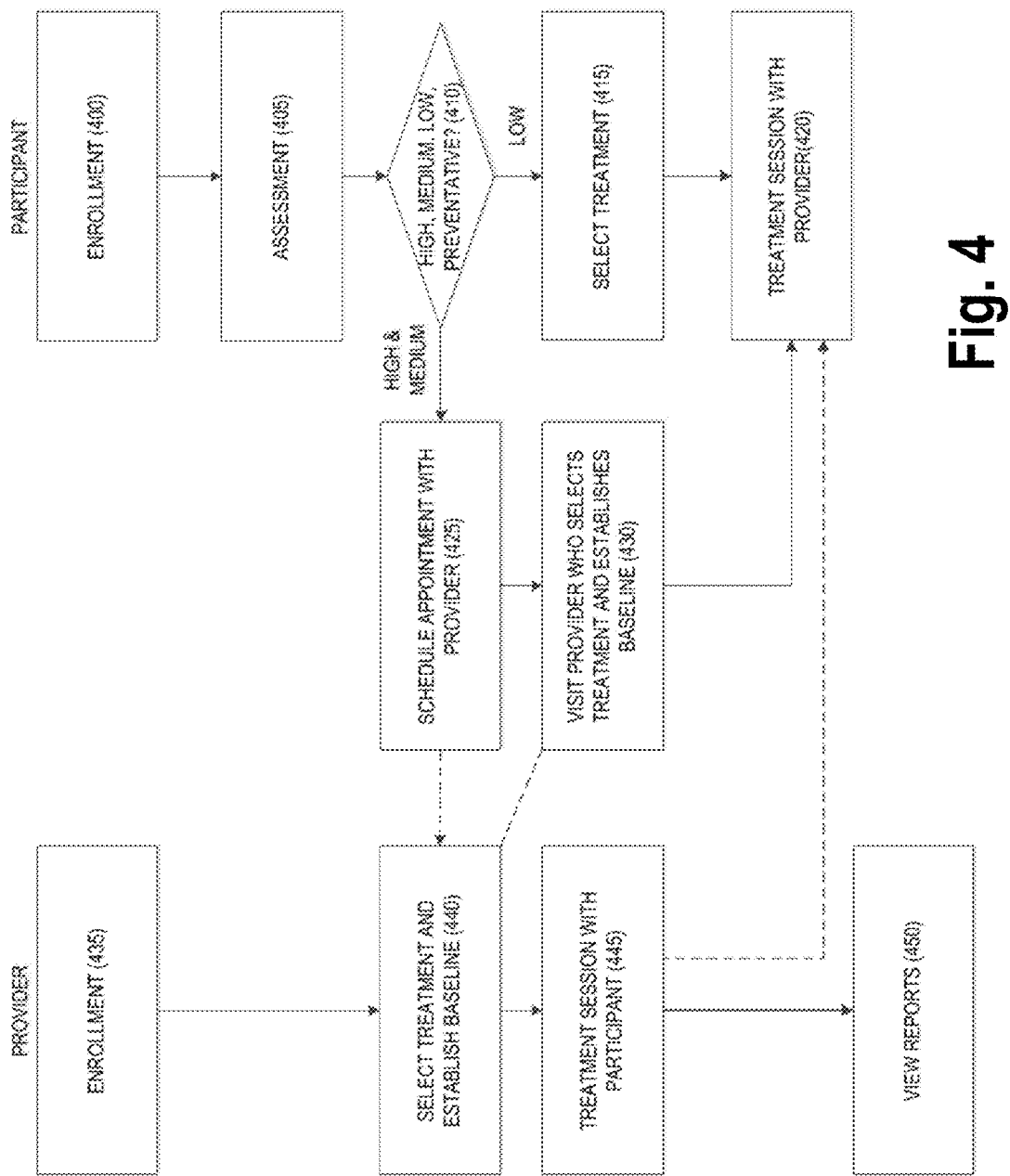
FIG. 4 is a flowchart illustrating operations and processes that can be used in accordance with various embodiments of the present invention.

Reference will now be made to FIGS. 4-16. FIG. 4 is a flowchart illustrating operations and processes that can be used in accordance with various embodiments of the present invention. And FIGS. 5-16 are exemplary input and output that can be produced by various embodiments of the present invention.

Participant Profiles

As noted, participants (users) may be health plan members, consumers, customers, patients, students, end users, and/or the like. In one embodiment, each participant may have one or more participant profiles accessible via the management computing entity 100. For example, a participant or someone on behalf of a participant (e.g., operating a participant computing entity 105 executing an appropriate application, display area, browser, dashboard, user interface, and/or the like) can input various information to register/enroll and create or update a participant profile for storage and use by the management computing entity 100 (Block 400 of FIG. 4). Such profiles can be created, stored, edited, and/or customized manually, automatically, and/or semi-automatically to adapt to various needs and circumstances.

In one embodiment, a participant (e.g., operating a participant computing entity 105) can input various information to be stored in association with the corresponding profile. Such information may include the participant's bibliographic data, such as the participant's name, gender, birthdate, age, text message addresses, languages spoken, phone numbers, postal address, social security number, and/or the like. Further, such information may include record numbers for the participant's electronic medical record (EMR), electronic health record (EHR), and/or personal health record (PHR). In one embodiment, the participant (e.g., operating a participant computing entity 105) can input medical data or such medical data can be semi-automatically or automatically retrieved by medical record data corresponding to the participant's surgeries, allergies, symptoms, medical conditions, primary care physician, specialist medical providers, health insurance information, health insurance authorizations (e.g., authorizations for durable medical equipment and/or outpatient surgery), medical claims, prescriptions, conditions, diagnoses, schedules, treatments, illnesses, concerns, insurance information, payment information, family history, and/or the like.

In some embodiments, the management computing entity 100 may also retrieve external data that may affect the participant's health and store the same in association with the participant's profile. Such external data may include data from various external data providers. Such data may include census data, state cancer profile data, disease outbreak data, chemical or toxic exposure data, demographic data, vital statistics data, and/or the like. The external data may also include weather-related data, such as data associated with thunderstorms, hurricanes, pollen levels, precipitation, cold fronts, heat waves, tornados, changes in barometric pressure, and/or the like. As will be recognized, external data may include data from various sources for a variety of reasons.

Provider Profiles

As noted, providers (users) may be doctors, physician assistants, insurance providers, care managers, health providers, trainers, coaches, therapists, physical therapists, healthcare-related professionals, teachers, and/or the like. In one embodiment, each provider may have one or more provider profiles accessible via the management computing entity 100. For example, a provider or someone on behalf of a provider (e.g., operating a provider computing entity 110 executing an appropriate application, display area, browser, dashboard, user interface, and/or the like) can input various information to register/enroll and create or update a provider profile for storage and use by the management computing entity 100 (Block 435 of FIG. 4). Such profiles can be created, stored, edited, and/or customized manually, automatically, and/or semi-automatically to adapt to various needs and circumstances.

In one embodiment, a provider (e.g., operating a provider computing entity 110) can input various information to be stored in association with the corresponding profile. Such information may include the provider's bibliographic data, such as the provider's name, gender, birthdate, age, languages spoken, phone numbers, postal address, and/or the like. In one embodiment, a provider profile may also include the provider's contract number, services provided, specialties, expertise, certifications, identification number, license numbers, and/or the like. As will be recognized, a variety of other approaches and techniques can be used to adapt to various needs and circumstances.

Assessments

In one embodiment, after creating a profile, participants can perform an assessment regarding surgeries, allergies, symptoms, medical conditions, prescriptions, conditions, diagnoses, illnesses, concerns, and/or the like (Block 405 of FIG. 4). In another embodiment, the assessment may occur before the participant enrolls. To do so, a participant (e.g., operating a participant computing entity 105 executing an appropriate application, display area, browser, dashboard, user interface, and/or the like in communication with the management computing entity 100) can perform the assessment. The assessment may allow for screening participants for specific conditions and/or indicators that are relevant in determining whether the participants should participate in specific care pathways, treatments, treatment plans, therapy plans, exercise regimens, exercises, therapies, programs, and/or the like (and/or whether they should make an appointment with a specific provider or type of provider).

As will be recognized, the management computing entity 100 may provide a variety of assessments for various conditions, complaints, diagnoses, illnesses, concerns, and/or the like. For example, a participant (e.g., operating a participant computing entity 105 in communication with the management computing entity 100) may first be prompted to identify the area of the body that is the primary concern. Or, the participant (e.g., operating a participant computing entity 105 in communication with the management computing entity 100) may be able to select from or input a variety of symptoms, such as back pain, headaches, breathing trouble, coughing, and/or the like. The management computing entity 100 can use the assessment as a funnel to narrow down the participant's concerns and identify the potentially appropriate treatments. For instance, assuming a participant has back pain, the participant (e.g., operating a participant computing entity 105) may perform an assessment designed with questions related to the back or shoulder. In this example, the concern is assumed to be related to a muscle-skeletal condition in the participant's shoulder. Thus, the management computing entity 100 can guide the participant (e.g., operating a participant computing entity 105) through the appropriate questions to properly classify or categorize the participant into a variety of categories and/or classifications. For example, a sample assessment may categorize or classify a participant as being preventative, low risk, medium risk, or high risk (Block 410 of FIG. 4). As will be recognized, a variety of other approaches and techniques can be used to categorize/classify participants to adapt to various needs and circumstances.

As noted, in one embodiment (much of which is shown in FIG. 5), the classification or categorization may be to group participants into one of four categories of risk: (1) preventive (not shown), (2) low risk; (3) medium risk; or (4) high risk. In one embodiment, for participants considered as being preventive or low risk, the management computing entity 100 may recommend that the participants self-treat for a period of time or until their symptoms continue or become worse. Such self-treatments may include remaining active, taking over-the-counter medications, watchfully waiting, applying hot or cold packs, and/or performing prescribed exercises or therapies (e.g., yoga, strength training, form training, and/or the like) guided by the management computing entity 100 and/or aided remotely by providers. For participants considered as being medium risk, the management computing entity 100 may recommend that they schedule a visit with a specific provide or a specific type of provider for treatment (e.g., manipulation, acupuncture, and/or the like), and/or provide a variety of other recommendations including performing prescribed exercises or therapies (e.g., physical therapies, occupational therapies, and/or the like). And for participants considered as high risk, the management computing entity 100 may recommend that the participants perform further assessments, schedule a visit with a specific provider or a specific type of provider for treatment (e.g., manipulation, acupuncture, and/or the like), and/or provide a variety of other recommendations. As will be recognized, the management computing entity 100 can provide a variety of recommendations to adapt to various needs and circumstances.

When scheduling an appointment with a provider is a recommendation, the management computing entity 100 can provide an appropriate application, display area, browser, dashboard, user interface, and/or the like for the participant (e.g., operating a participant computing entity 105) to schedule an appointment with the recommended provider or type of provider (Block 425 of FIG. 4). For example, based on the assessment, the management computing entity 100 may identify the types of providers in the participant's geographic area. Thus, through the appropriate application, display area, browser, dashboard, user interface, and/or the like, both the participant (e.g., operating a participant computing entity 105) and the provider (e.g., operating a provider computing entity 110) can correspond with one another through the management computing entity 100 to perform a variety of tasks—including scheduling appointments.

In one embodiment, in scenarios in which the management computing entity 100 recommends that the participant meet with a provider before or instead of selecting or performing a selected or prescribed treatment, the participant may meet with the provider via an in-person visit, interactive session, and/or the like. During the consultation with the provider, the provider may review the participant's assessment, perform further assessments, conduct an initial examination, and/or the like. If warranted, the provider (perhaps with the assistance of the participant) may prescribe an appropriate care pathway, treatment, treatment plan, therapy plan, exercise regimen, therapy, program, and/or the like for the participant (Blocks 430 and 440 of FIG. 4). In certain embodiments, the provider may also establish or create a baseline for the participant (Blocks 440 and 430 of FIG. 4). The baseline can simply be the participant's current state with regard to a condition or selected treatment (e.g., current range of motion).

Figure 6:
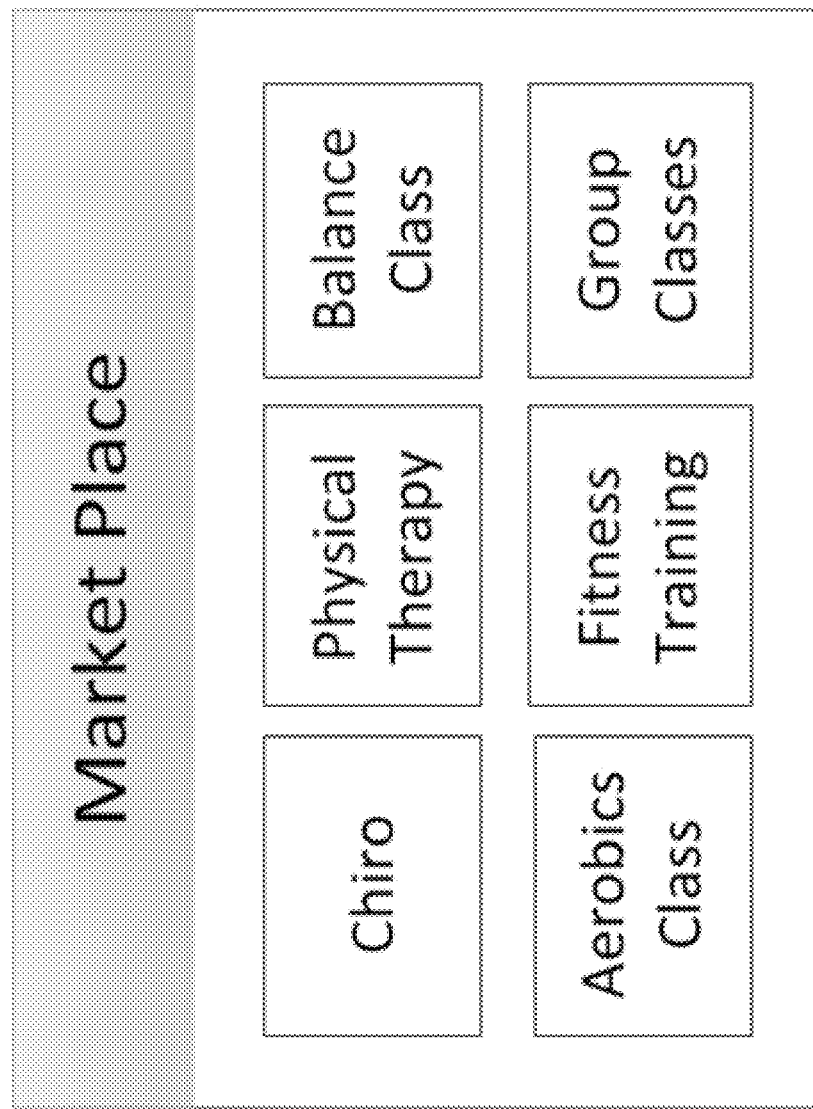
Figure 7:
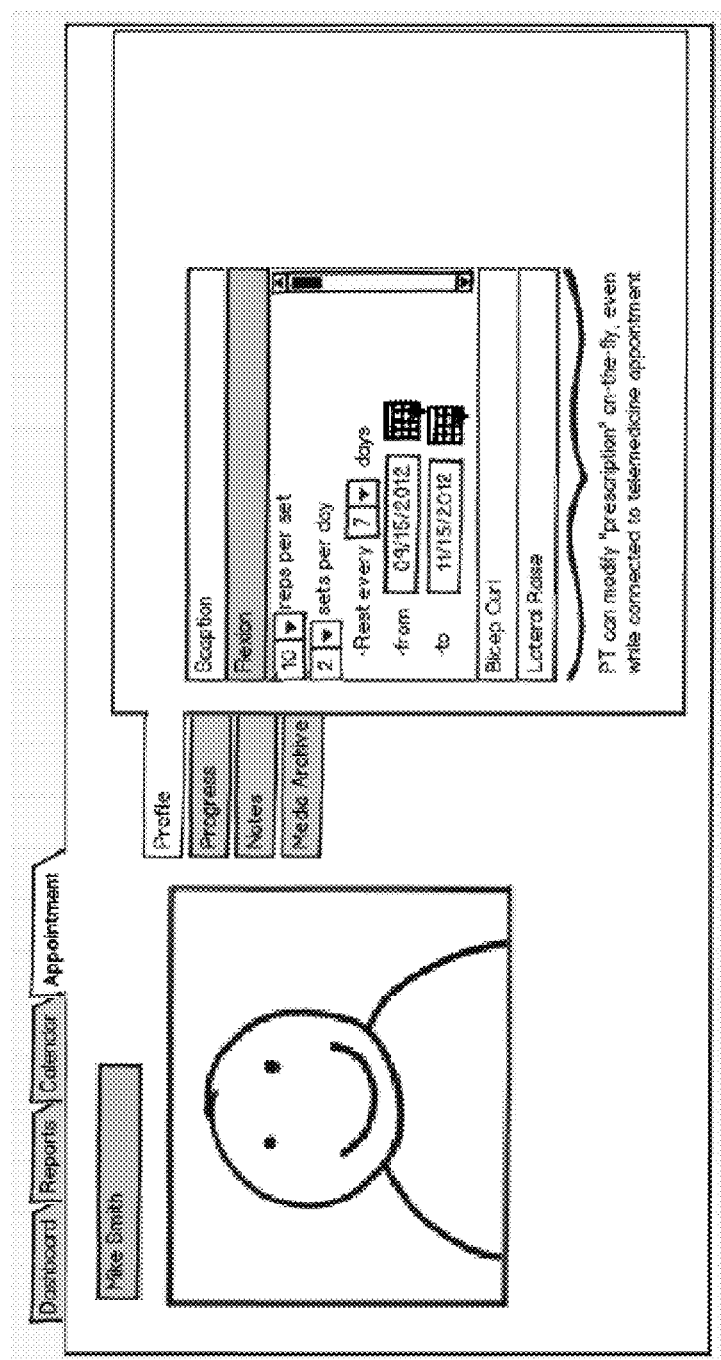
Figure 8:
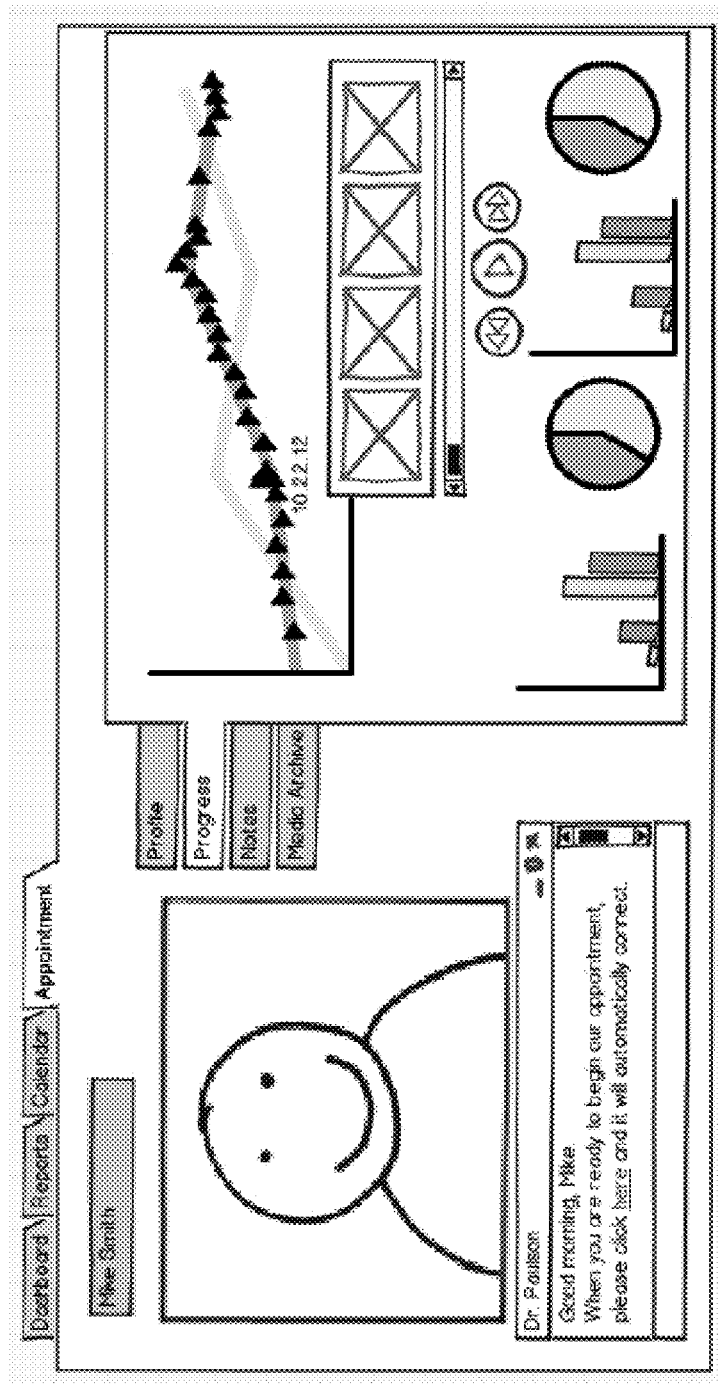
Figure 9:
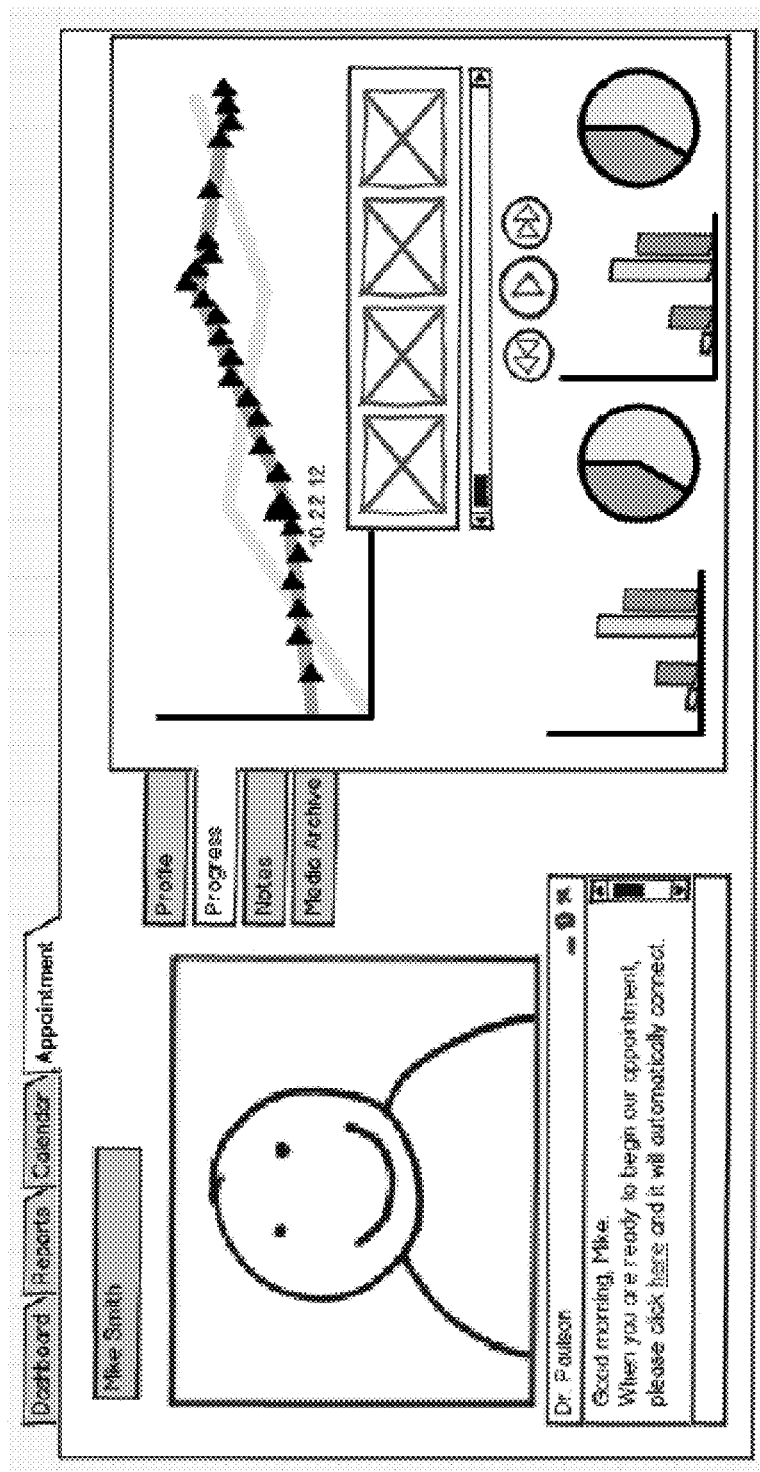
Figure 10:
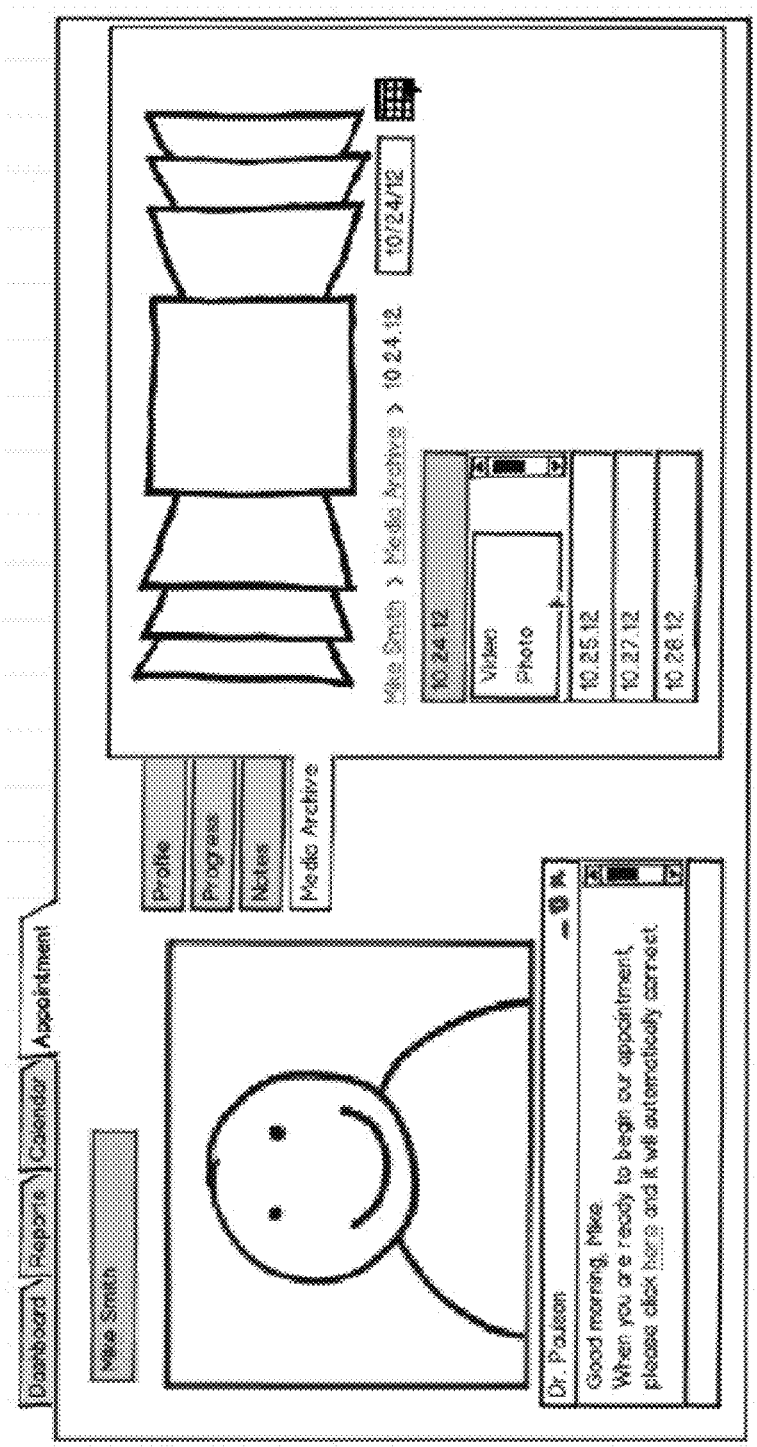
Figure 11:
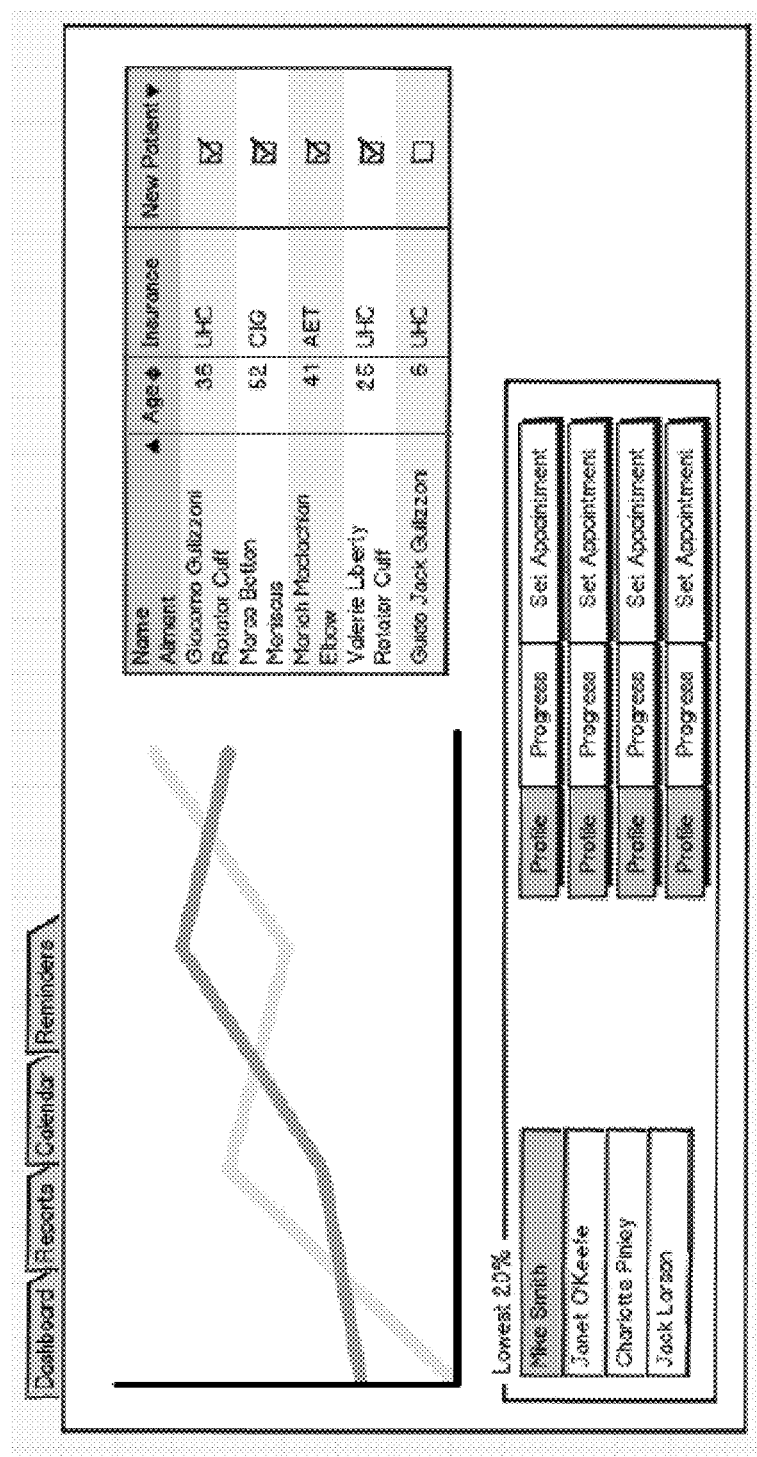
Figure 12:
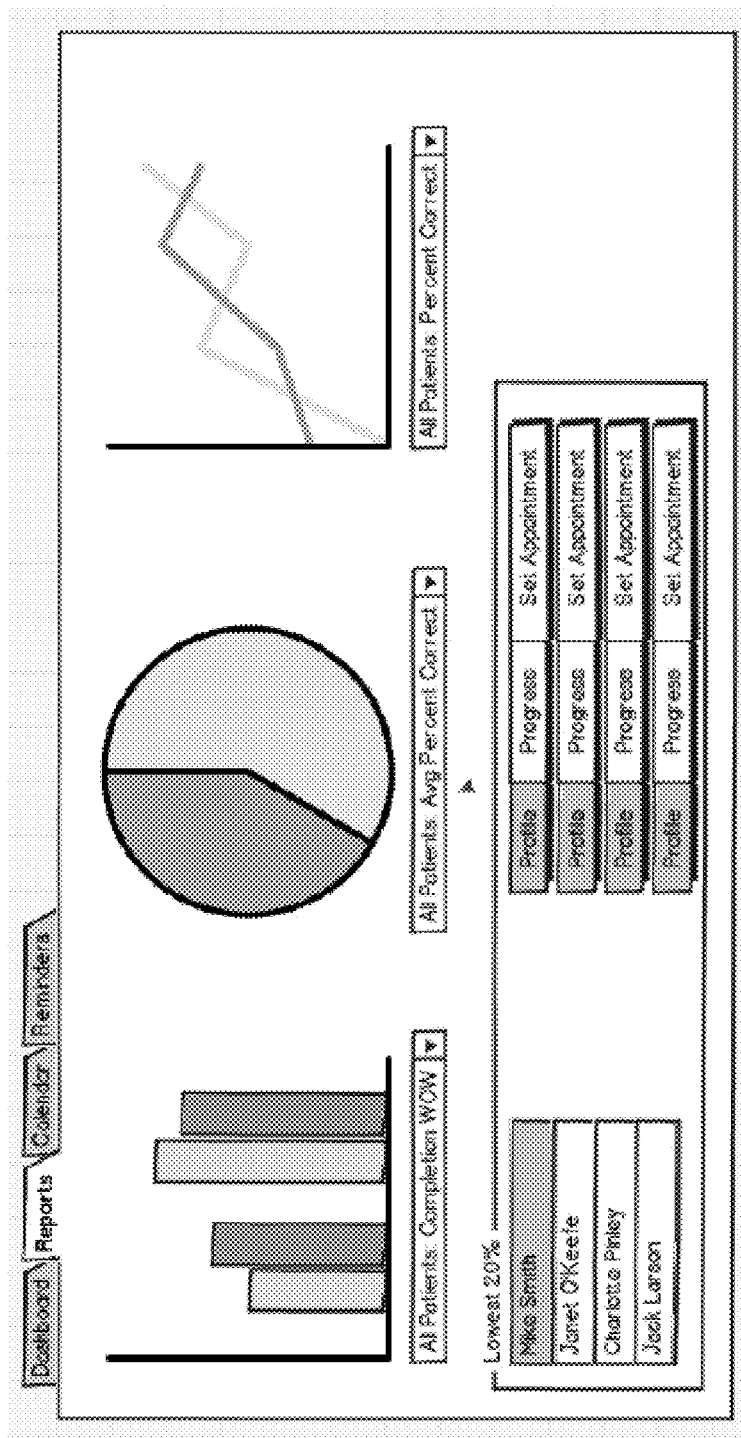

In one embodiment, as appropriate, the management computing entity 100 can also provide the recommended care pathways, treatments, treatment plans, therapy plans, exercise regimens, exercises, therapies, programs, and/or the like from which the participant (e.g., operating a participant computing entity 105) can choose. The management computing entity 100 can provide the care pathways, treatments, treatment plans, therapy plans, exercise regimens, exercises, therapies, programs, and/or the like based on the assessment for a given participant to address the participant's concern. For example, as shown in FIG. 6, the participant (e.g., operating a participant computing entity 105 in communication with a management computing entity 100) may be able to access a marketplace from which he or she can browse and select at least one care pathway, treatment, treatment plan, therapy plan, exercise regimen, therapy, program, and/or the like (Block 415 of FIG. 4). As will be recognized, a variety of other approaches and techniques can be used to adapt to various needs and circumstances.

Sessions

In one embodiment, after either a participant or provider selects an appropriate care pathway, treatment, treatment plan, therapy plan, exercise regimen, therapy, program, and/or the like, the participant (e.g., operating a participant computing entity 105) can perform the same—including at locations remote from the provider and/or at times convenient to the participant. Such remote locations may be in the participant's home or any other location in which the participant has access to an appropriate participant computing entity 105 (Block 420 of FIG. 4). To perform such treatments, participants (e.g., operating participant computing entities 105) may need to download, for example, a video of the selected or prescribed treatment and an avatar (e.g., to model the exercise or treatment). Or, the participant (e.g., operating a participant computing entity 105) may be able to access the same via an appropriate application, display area, browser, dashboard, user interface, and/or the like. As will be recognized, such treatments may include videos (and avatars modeling the exercises) that are to be followed, slide pictures with corresponding audio or text that are to be followed, and/or the like.

In one embodiment, as described, participants (e.g., operating participant computing entities 105) can perform selected or prescribed treatments without interaction with a provider (e.g., doctor, physician assistant, insurance provider, care manager, health provider, trainer, coach, therapist, physical therapist, healthcare-related professional, teacher, and/or the like). Such non-interactive or non-live sessions can be recorded by the participant computing entity 105 locally and transmitted/provided to the management computing entity 100 for storage. The management computing entity 100 may provide such session files/recordings via the interfaces for both provider and participant access as will be described. As will be recognized, a variety of other approaches and techniques can be used to adapt to various needs and circumstances.

In another embodiment, the selected or prescribed treatments may be performed in real time or near real time with a provider (e.g., operating a provider computing entity 110) interacting with the participant (e.g., operating a participant computing entity 105) during the same. Such interactions (whether in real time or not) may include feedback, status changes, encouragement, and/or a variety of other verbal and non-verbal interactions from the corresponding providers (Block 445 of FIG. 4).

Regardless of whether the sessions are with or without real time interaction with a provider, the management computing entity 100 may enable providers to review information associated with participants, their medical history, treatments, and/or the like. For instance, a provider (e.g., operating a provider computing entity 110 in communication with a management computing entity 100) may have the ability to review a participant's profile using an "Appointment" tab during a real-time session/interaction with a participant or before or after a session/interaction (see FIGS. 7-12). Through an appropriate application, display area, browser, dashboard, user interface, and/or the like, the provider (e.g., operating a provider computing entity 110) can access a participant's media archive (e.g., previously performed and recorded treatments). Through the media archive, the provider (e.g., operating a provider computing entity 110) may access different video, audio, and/or motion capture (e.g., skeleton) files to view or review the same regarding a participant's treatment. The profile, for example, may include the participant's selected or prescribed treatment. Further, a "Notes" tab may enable the provider (e.g., operating a provider computing entity 110) to create and manage participant notes which can be stored in association with the participants' record and be exported to the participant's EMR, PHR, EHR, and/or the like. From a "Progress" tab, for example, a provider (e.g., operating a provider computing entity 110) may view graphs that represent session activity over a period of time (see FIGS. 8 and 9). The session activity may represent a participant's progress (such as flexibility, exercise time, and/or the like) that correspond to the participant's individual sessions. In one embodiment, "Play" images or icons in the Progress tab may be a link or pointer to a corresponding media file for the represented session. As noted, this may allow the provider (e.g., operating a provider computing entity 110) to view and review various sessions performed by the participant and recorded and stored by the management computing entity 100. For instance, while hovering over, clicking on, or otherwise selecting the play button, the provider computing entity 110 may cause display of a popup window of photos and videos from sessions during key points. Such key points may be the start of a session, the middle of a session, the end of a session, major or minor errors in exercise during a session, and/or the like. Through the appropriate application, display area, browser, dashboard, user interface, and/or the like, the provider (e.g., operating a provider computing entity 110) may be able to modify a participant's selected or prescribed treatment plan at any time, even during a real-time session with the participant. As will be recognized, a variety of other approaches and techniques can be used to provide providers with access to medical history, treatment, and/or other information for participants.

Figure 13:
Figure 14:
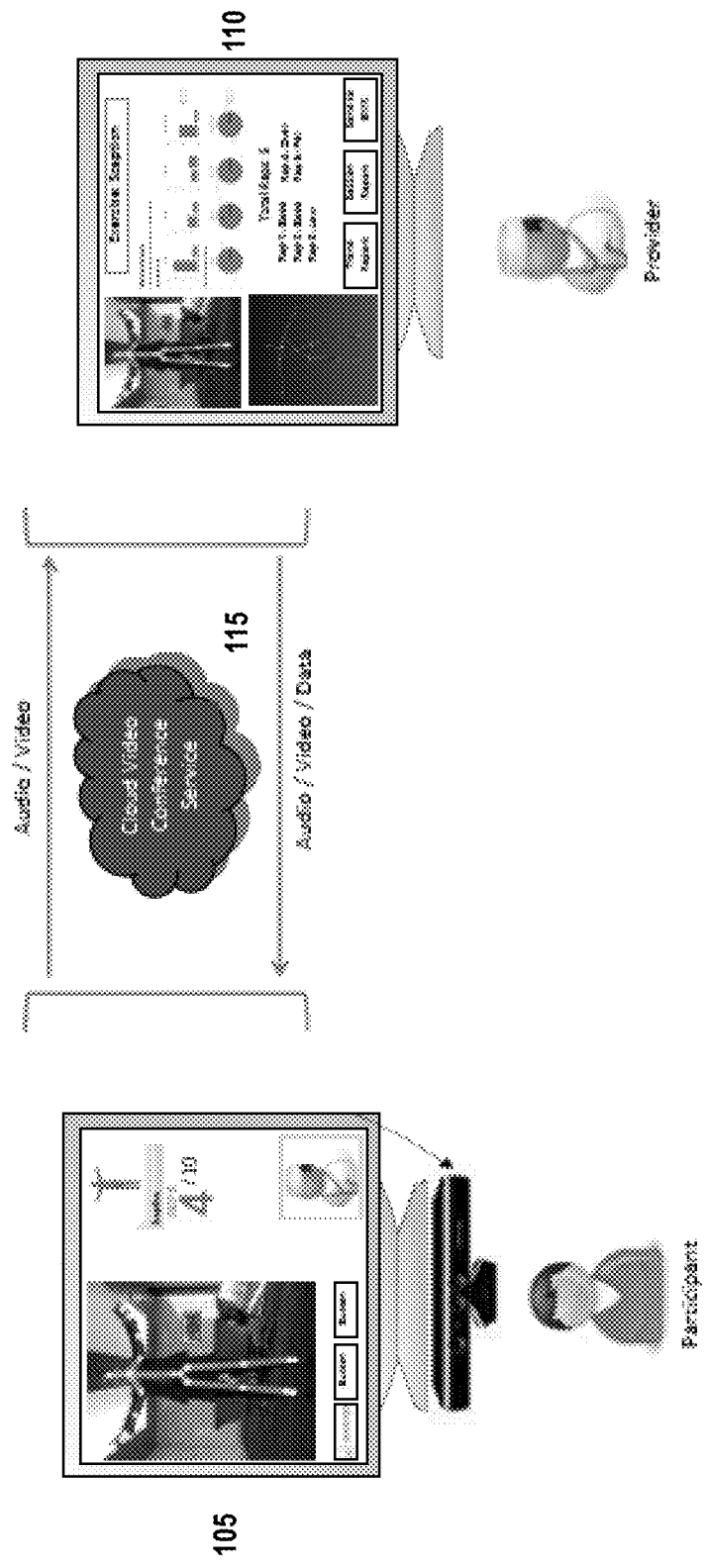
Figure 15:
Figure 16:
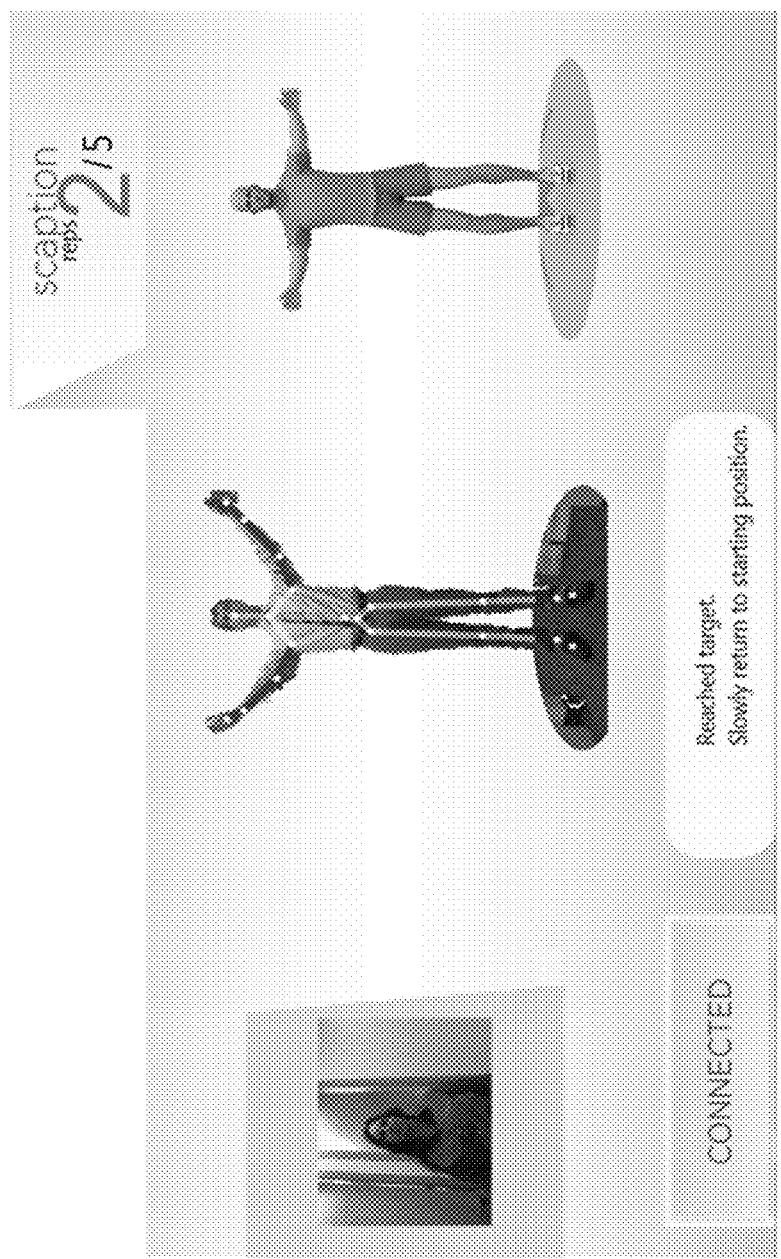

As noted, treatments can be interactive or real-time sessions with providers. To begin such interactive or real-time sessions, the parties (e.g., operating the appropriate computing entities 105, 110) may initiate or launch their respective applications, browsers, display areas, dashboards, user interfaces, and/or the like. For example, FIG. 13 shows a "Connect to Doctor" image or icon that can be selected by a participant (e.g., operating a participant computing entity 105) to initiate a live or interactive session for treatment with a provider (e.g., operating a provider computing entity 110). The management computing entity 100 may also provide similar functionality for the provider. As will be recognized, the connectivity of such sessions can be controlled and coordinated through the management computing entity 100. In certain embodiments, this may initiate a session between the parties that has to be accepted by the party not initiating the session. Depending on the embodiment, the management computing entity 100 may establish sessions between the appropriate computing entities. In one embodiment, establishing an interactive session may refer to the management computing entity 100 initiating and maintaining/managing the interactive session between the provider computing entity 110 and the participant computing entity 105 (e.g., the data flowing through the management computing entity 100). In other embodiment, establishing an interactive session may refer to the management computing entity facilitating or brokering the interactive session between the provider computing entity 110 and the participant computing entity 105 (e.g., the data flowing to the respective entities in a peer-to-peer configuration). As will be recognized, the management computing entity 100 can use a variety of approaches and techniques to establish interactive sessions. Once a session is established, the participant can perform the selected or prescribed treatments for the provider, and the provider can provide feedback, encouragement, and/or a variety of other verbal and non-verbal interactions to the participant during the treatment. FIG. 14 shows a live or interactive session between a participant (e.g., operating a participant computing entity 105) and a provider (e.g., operating a provider computing entity 110).

Although not shown, it will be recognized, a provider (e.g., operating a provider computing entity 110) may conduct multiple live treatments with various participants simultaneously. For instance, a provider in Atlanta, Ga. may schedule and conduct live treatments with (1) a participant in London, England, (2) a participant in Seattle, Wash., and (3) a participant in Dalton, Ga., all at the same time. Thus, the appropriate application, display area, browser, dashboard, user interface, and/or the like may provide the provider with the ability to interact with multiple participants each of whom is performing interactive treatments with the provider at locations remote from the provider at the same time. Further, as previously described, participant (e.g., operating a participant computing entity 105) can interact with multiple providers via the same—e.g., interacting with their chiropractors, physical therapists, primary care physician, and/or the like.

In one embodiment, from the participant side during a real-time session, the participant computing entity 105 (e.g., in communication with the management computing entity 100) can cause display of the treatment the participant is to perform, such as showing/playing a video that is to be followed, triggering an avatar demonstration slide pictures with corresponding audio or text that are to be followed, and/or the like. The management computing entity 100 may also remotely alter either in real-time or in downloadable fashion exercise configurations for such parameters as motion ranges, heights, angles, motion repetition counts and/or the like. As the participant computing entity 105 causes display of the treatment the participant is to perform, the participant performs (e.g., mimics, copies, or simulates) the motions, movements, steps, and/or the like for the treatment. The participant (e.g., operating a participant computing entity 105) may be able to pause, rewind, forward, and/or resume the session at any time, such as for discussion with the provider.

In one embodiment, in addition to causing display of the treatment plan, the participant computing entity 105 can capture the participant's audio data (e.g., audio captured by the participant computing entity 105), video data (e.g., video captured by the participant computing entity 105), and motion data (e.g., motion captured by the participant computing entity 105) at substantially the same time (the term substantially used to account for minor variations in processing). For example, the audio and video (e.g., audio and video data) captured by the participant computing entity 105 may simply be recordings of the participant as he or she performs the treatment. The motion (e.g., motion data) captured by the participant computing entity 105 during the treatment may correspond to the participant's physical positions. The motion data, for example, may represent the participant's movements, angles, repetitions, and/or the like using various points corresponding to the participant's body. For instance, exemplary points that may be captured by the participant computing entity 105 via the motion data are provided below in Table 1.

TABLE 1

| Joint |
|---|
| Head |
| Neck |
| Torso |
| Waist |
| Left Collar |
| Left Finger |
| Left Shoulder |
| Left Elbow |
| Left Wrist |
| Left Hand |
| Left Fingertip |
| Right Collar |
| Left Thumb |
| Right Shoulder |
| Right Elbow |
| Right Wrist |
| Right Hand |
| Right Fingertip |
| Left Hip |
| Right Finger |
| Left Knee |
| Left Ankle |
| Left Foot |
| Right Hip |
| Right Knee |
| Right Ankle |
| Right Thumb |
| Right Foot |

Table 1 is not an exhaustive list of captured points or data, but is simply illustrative in nature. As will be recognized, further points and data can be captured—including pulse rates and/or the like. With various points and data captured, a skeleton representative of the participant's movements, angles, repetitions, and/or the like can be created by connecting the appropriate points. For instance, a skeleton can be created or generated from the motion data by connecting the head point to the neck point, the right ankle point to the right foot point, and so on. With the skeleton, various computing entities can cause display of the skeleton that represents the participant's movements, angles, repetitions, and/or the like during the treatment. For instance, as shown in FIG. 13, the treatment (e.g., via video, slides, text, avatars, exercises, audio, and/or the like) may provide an indication to the participant (e.g., operating a participant computing entity 105) to raise his or her arms (with thumbs up) to shoulder level in the scapular plane (45° diagonal) and to then lower the arms slowly. Simultaneously, the participant computing entity 105 can cause display of the user performing the same via the video and the skeleton superimposed on the video (see FIGS. 13, 14, and 16). The management computing entity 100 can also monitor the participant's progress (e.g., whether the appropriate angles were achieved, the length of time required to complete the treatment, whether and when the treatment was completed, the repetitions of requested movements, and/or the like) and alter the parameters of those exercises as required.

In one embodiment, the participant computing entity 105 or management computing entity 100 can also record such data captured at substantially the same time (to account for minor variations in processing) locally in one or more files and/or transmit the same to the management computing entity 100 and/or the provider computing entity 110 for storage, playback, viewing, and/or the like. For instance, as described, the management computing entity 100 can store such files for access by providers and/or participants as described above. In an interactive or real-time context, the participant computing entity 105 may also stream/transmit/provide the audio data, video data, and motion data as a combined data stream (e.g., with the audio, video, and motion synchronized). In another embodiment, the participant computing entity 105 can stream/transmit/provide the audio data and video data as a combined data stream (e.g., with the audio and video synchronized) and stream/transmit/provide the motion data as a separate data stream (e.g., not synchronized to the audio and video data). And in yet another embodiment, the participant computing entity 105 can stream/transmit/provide the audio data, video data, and motion data captured at substantially the same time as separate, individual data streams (e.g., not synchronized). In one embodiment, the participant computing entity 105 can stream/transmit/provide such data streams to the management computing entity 100 for transmission to the appropriate provider computing entity 110. In another embodiment, the participant computing entity 105 can stream/transmit/provide such data streams to the appropriate provider computing entity 110 facilitated by the management computing entity—e.g., broker the streams in a peer-to-peer communication between the appropriate provider computing entity 110 and the appropriate participant computing entity 105.

In one embodiment, in the interactive or live context, the provider computing entity 110 can receive the audio data, video data, and/or motion data directly or indirectly from the management computing entity 100 and/or the participant computing entity 105. After receiving such data, the appropriate computing entity (e.g., management computing entity 100 and/or provider computing entity 110) can cause simultaneous (and separate or combined) display, of both the video (e.g., captured video data) and the skeleton (e.g., captured motion data)—see FIG. 15 for a separate display and see FIGS. 13 and 16 for a combined display. The appropriate computing entity (e.g., management computing entity 100 and/or provider computing entity 110) can also play the received audio. In the example shown in FIG. 15, the video (e.g., streamed video data) and the skeleton (e.g., streamed motion data) are displayed simultaneously via separate panes, windows, display areas, interfaces, browsers, dashboards, applications, and/or the like. However, as will be recognized, the video (e.g., streamed video data) and the skeleton (e.g., streamed motion data) can be combined and/or displayed simultaneously in a single pane, window, display area, interface, browser, dashboard, application, and/or the like—see FIGS. 13 and 16. This may be the case whether such streams are transmitted and received as separate or combined streams. Thus, as the motion data representing the participant's movements, angles, repetitions, and/or the like is displayed, the corresponding video can be simultaneously displayed via a single or separate pane or window. In one embodiment, to facilitate an embodiment of separate displays, separate streams for the participant's video data and motion data may be desired. This may allow the transmitting/streaming computing entity to stream the data without creating a combined data stream and appropriately synchronizing the data. It may also allow the receiving computing entity to simply receive separate streams and simultaneously display the same. In one embodiment, any of the computing entities may select and allow for providers and/or participants to enable or disable the motion capture (e.g., skeleton). As will be recognized, a variety of other approaches and techniques can be used to adapt to various needs and circumstances.

Similarly, the provider computing entity 110 can provide/transmit video and audio data to the participant computing entity 105 (e.g., via the management computing entity 100) as described above with regard to the participant computing entity 105. Thus, the video data and audio data from the provider computing entity 110 may be provided to the participant computing entity 105 in a combined data stream or separate video and audio streams. Upon receipt of the appropriate data streams (e.g., via the management computing entity 100), the participant computing entity can play audio and/or cause display of the video of the provider while the participant is performing the selected or prescribed treatment (see FIGS. 14 and 16). Thus, there is a two-way stream for between the computing entities (e.g., whether a direct peer-to-peer stream or an indirect stream through the management computing entity 100). As will be recognized, a variety of other approaches and techniques can be used to adapt to various needs and circumstances.

Such embodiments can be used to establish interactive or real-time sessions between participants (e.g., operating participant computing entities 105) and providers (e.g., operating provider computing entities 110)—Blocks 420 and 445 of FIG. 4. Through such interactive or real-time sessions, providers can provide verbal and non-verbal feedback, encouragement, and/or the like. Similarly, the appropriate application, display area, browser, dashboard, user interface, and/or the like can enable the provider to document such sessions. As also noted, the provider (e.g., operating a provider computing entity 110) may be provided with the ability to pause, rewind, forward, and/or resume the session to provide feedback to the participant, adjust the selected or prescribed therapy (for immediate effect on the participant side), take notes regarding the session, and/or the like.

In one embodiment, the provider (e.g., operating a provider computing entity 110 in communication with a management computing entity 100) may be able to generate, access, or view various reports for participants (Block 450 of FIG. 4). Such reports may include snapshot of failed movements (e.g., movements that do not meet a configurable threshold), repetition counts, bar graphs, line graphs, pie charts, completion percentage, and/or the like related to one or more of a participant's sessions. As will be recognized, a variety of other reporting approaches and concepts can be used to adapt to various needs and circumstances.

IV. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method, the method comprising:
   establishing, via one or more processors of a provider computing entity, an interactive session with a participant computing entity, wherein the interactive session is for a user of the participant computing entity to perform a treatment during the interactive session;
   receiving, via one or more processors of the provider computing entity, a video stream of video data of the interactive session and a motion stream of motion data of the interactive session, (a) the video data and the motion data captured simultaneously by and originating from the participant computing entity, (b) the video data comprising video of the user performing the treatment during the interactive session, and (c) the motion data comprising points representative of the user's body parts appropriately connected forming a skeleton representative (i) of the user and (ii) of the user's movements performing the treatment during the interactive session, and providing, via one or more processors of the provider computing entity, for simultaneous and separate display (a) of at least a portion of the video data comprising the video of the user performing the treatment during the interactive session in a first display area of a display and (b) of at least a portion of the motion data comprising points representative of the user's body parts appropriately connected forming a skeleton representative (i) of the user and (ii) of the user's movements performing the treatment during the interactive session in a second display area of the display, wherein the first display area and the second display do not overlap.

2. The method of claim 1, wherein the participant computing entity enables the participant to conduct interactive sessions with a plurality of providers.

3. The method of claim 1, wherein the provider computing entity enables the provider to conduct interactive sessions with a plurality of participants.

4. The method of claim 1, wherein the interactive session further comprises an audio stream of audio data originating from the participant computing entity and provided to the provider computing entity.

5. The method of claim 1, wherein the interactive session further comprises a video stream of video data and an audio stream of audio data originating from the provider computing entity and provided to the participant computing entity.

6. A provider apparatus comprising at least one processor and at least one memory including computer program code, the at least one memory and the computer program code configured to, with the processor, cause the provider apparatus to at least:

establish an interactive session with a participant computing entity, wherein the interactive session is for a user of the participant computing entity to perform a treatment during the interactive session;

receive a video stream of video data of the interactive session and a motion stream of motion data of the interactive session, (a) the video data and the motion data captured simultaneously by and originating from the participant computing entity, (b) the video data comprising video of the user performing the treatment during the interactive session, and (c) the motion data comprising points representative of the user's body parts appropriately connected forming a skeleton representative (i) of the user and (ii) of the user's movements performing the treatment during the interactive session; and provide for simultaneous and separate display (a) of at least a portion of the video data comprising the video of the user performing the treatment during the interactive session in a first display area of a display and (b) of at least a portion of the motion data comprising points representative of the user's body parts appropriately connected forming a skeleton representative (i) of the user and (ii) of the user's movements performing the treatment during the interactive session in a second display area of the display, wherein the first display area and the second display do not overlap.

7. The provider apparatus of claim 6, wherein the participant computing entity enables the participant to conduct interactive sessions with a plurality of providers.

8. The provider apparatus of claim 6, wherein the provider apparatus enables the provider to conduct interactive sessions with a plurality of participants.

9. The provider apparatus of claim 6, wherein the interactive session further comprises an audio stream of audio data originating from the participant computing entity and provided to the provider apparatus.

10. The provider apparatus of claim 6, wherein the interactive session further comprises a video stream of video data and an audio stream of audio data originating from the provider apparatus and provided to the participant computing entity.

11. A computer program product, the computer program product comprising at least one non-transitory computer-readable storage medium having computer-readable program code portions stored therein, the computer-readable program code portions executable by a provider computing entity and comprising:

an executable portion configured to establish an interactive session with a participant computing entity, wherein the interactive session is for a user of the participant computing entity to perform a treatment during the interactive session;

an executable portion configured to receive a video stream of video data of the interactive session and a motion stream of motion data of the interactive session, (a) the video data and the motion data captured simultaneously by and originating from the participant computing entity, (b) the video data comprising video of the user performing the treatment during the interactive session, and (c) the motion data comprising points representative of the user's body parts appropriately connected forming a skeleton representative (i) of the user and (ii) of the user's movements performing the treatment during the interactive session; and an executable portion configured to provide for simultaneous and separate display (a) of at least a portion of the video data comprising the video of the user performing the treatment during the interactive session in a first display area of a display and (b) of at least a portion of the motion data comprising points representative of the user's body parts appropriately connected forming a skeleton representative (i) of the user and (ii) of the user's movements performing the treatment during the interactive session in a second display area of the display, wherein the first display area and the second display do not overlap.

12. The computer program product of claim 11, wherein the participant computing entity enables the participant to conduct interactive sessions with a plurality of providers.

13. The computer program product of claim 11, wherein the provider computing entity enables the provider to conduct interactive sessions with a plurality of participants.

14. The computer program product of claim 11, wherein the interactive session further comprises an audio stream of audio data originating from the participant computing entity and provided to the provider computing entity.

15. The computer program product of claim 11, wherein the interactive session further comprises a video stream of video data and an audio stream of audio data originating from the provider computing entity and provided to the participant computing entity.

* * * * *